United States Patent [19]
Jans et al.

[11] Patent Number: 5,759,580
[45] Date of Patent: Jun. 2, 1998

[54] COMPOSITIONS CONTAINING MICRONIZED NEBIVOLOL

[75] Inventors: Eugeen Marie Jozef Jans, Meerhout; Guido Franciscus Smans, Lille; Paul Marie Victor Gilis, Beerse, all of Belgium

[73] Assignee: Janssen Pharmaceutica, N.V., Beerse, Belgium

[21] Appl. No.: 669,415

[22] PCT Filed: Feb. 10, 1995

[86] PCT No.: PCT/EP95/00489

§ 371 Date: Jul. 9, 1996

§ 102(e) Date: Jul. 9, 1996

[87] PCT Pub. No.: WO95/22325

PCT Pub. Date: Aug. 24, 1995

[51] Int. Cl.$^6$ .................................................. A61K 9/14
[52] U.S. Cl. ..................... 424/489; 424/494; 424/488; 424/480; 424/461; 424/470; 424/1.13
[58] Field of Search .......................... 424/489, 490, 424/461, 470, 1.13, 46

[56] References Cited

FOREIGN PATENT DOCUMENTS

| 145067 | 11/1984 | European Pat. Off. |
| 334429 | 3/1989 | European Pat. Off. |

*Primary Examiner*—Thurman K. Page
*Assistant Examiner*—William E. Benston, Jr.
*Attorney, Agent, or Firm*—Ellen Ciambrone Coletti

[57] ABSTRACT

The present invention relates to pharmaceutical compositions containing as active ingredient micronized nebivolol of formula (I) and ways of preparing said compositions.

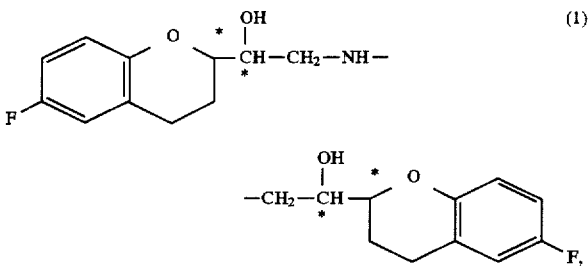

20 Claims, No Drawings

COMPOSITIONS CONTAINING MICRONIZED NEBIVOLOL

CROSS-REFERENCE TO RELATED APPLICATIONS

This application is based upon PCT application Ser. No. PCT/EP 95/00489, filed Feb. 10, 1995, which claims priority from U.S. patent application Ser. No. 08/197,988, filed on Feb. 17, 1994.

The present invention relates to pharmaceutical compositions comprising as active ingredient a micronized form of solid nebivolol or a pharmaceutically acceptable acid addition salt thereof and ways of preparing said compositions.

Nebivolol is the generic name of (±)-[R*[S*[S*-(S*)]]]-α,α'-[iminobis(methylene)bis-[6-fluoro-3,4-dihydro-2H-1-benzopyran-2-methanol]. The general structure of nebivolol is shown as formula (I). The structure of formula (I) has four stereogenic centers which are each indicated with an asterisk.

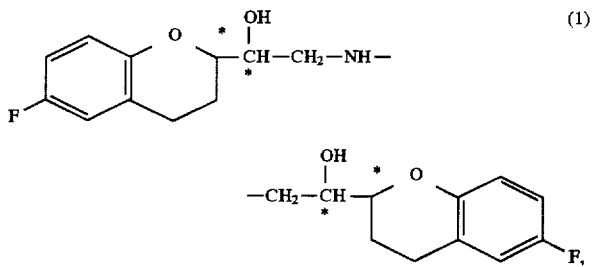

Nebivolol is a mixture of equal amounts of 2 enantiomers having respectively the SRRR- and the RSSS-configuration. The SRRR-configuration is referred to as $SR_3$-nebivolol (d-nebivolol) and the RSSS-configuration is referred to as $RS_3$-nebivolol (l-nebivolol). $SR_3$-nebivolol is a potent and selective $\beta_1$-adrenergic antagonist both in vitro and in vivo. Nebivolol can be distinguished from other β-adrenergic antagonists because it acutely lowers blood pressure in spontaneously hypertensive rats, decreases total peripheral vascular resistance and augments stroke volume in anaesthetised dogs. These haemodynamic effects are largely attributable to $RS_3$-nebivolol. It was also discovered that $RS_3$-nebivolol is a potentiator for a series of antihypertensive agents such as atenolol, propanolol, prazosin, hydralazine and, interestingly, also its own enantiomer, i.e. $SR_3$-nebivolol. Several clinical trials have also demonstrated the therapeutic potential of nebivolol as a $\beta_1$-selective betablocker and antihypertensive agent.

EP-0,145,067 generally describes 2,2'-iminobisethanol derivatives useful for the treatment and/or prevention of disorders of the coronary vascular system. EP-0,334,429 describes [iminobismethylene]bis[3,4-dihydro-2H-1-benzopyran-2-methanol]derivatives including nebivolol.

Nebivolol may be prepared according to the procedures described in EP-0,145,067 and more specifically in EP-0,334,429. Nebivolol has basic properties and may be converted into its pharmaceutically acceptable acid addition salt forms by treatment with appropriate acids. Appropriate acids are, for example, inorganic acids, such as hydrohalic acid, e.g. hydrochloric, hydrobromic and the like, and sulfuric acid, nitric acid, phosphoric acid; or organic acids, for example, acetic, propanoic, hydroxyacetic, 2-hydroxypropanoic, 2-oxopropanoic, ethanedioic, propanedioic, butanedioic, (Z)-2-butenedioic, (E)-2-butenedioic, 2-hydroxybutanedioic, 2,3-dihydroxybutanedioic, 2-hydroxy-1,2,3-propanetricarboxylic, methanesulfonic, ethanesulfonic, benzenesulfonic, 4-methylbenzenesulfonic, cyclohexanesulfamic, 2-hydroxybenzoic, 4-amino-2-hydroxybenzoic and the like acids. The acid addition salt that is preferred in this invention is the hydrochloride acid addition salt.

Pharmaceutical compositions according to the present invention are solid or semi-solid pharmaceutical compositions. Interesting solid pharmaceutical compositions are, for instance, powders, pills, capsules, tablets and the like. The term "semi-solid pharmaceutical composition" refers to pharmaceutical compositions substantially consisting of a dispersion of solid active ingredient in a (highly) viscous formulating agent. Interesting semi-solid pharmaceutical compositions are, for instance, suppositories, creams, gels, ointments and the like.

Interesting solid pharmaceutical compition is a single-unit dosage form, i.e. a non-multi-particulate dosage form.

The solid dosage form that is preferred within the present invention is a tablet. The person skilled in the art has to take into account the characteristics of tablets while searching for a composition. Specific characteristics of tablets are shape, disintegration time, and particularly hardness.

Oral administration constitutes the generally preferred route for administration of pharmaceuticals since this route is particularly convenient and acceptable to patients. However, preparing a solid dosage form for oral administration having all the correct characteristics sometimes forms a serious challenge for a person skilled in the art of preparing pharmaceutical compositions. In order for a substance to be effective, it has to reach appropriate concentrations in the bloodstream of the patient within an acceptable time after intake. In other words the substance has to have an acceptable bioavailability.

A very important factor influencing the bioavailability of substances after oral intake is the dissolution, i.e. the rate of dissolving of the substance, particularly in gastric fluid. It is recognized that the dissolution for the solid dosage form of the present invention should amount to at least 75% in 45 minutes in 0.1N HCl at a temperature of 37° C. Said dissolution is measured according to the test procedure described in example 5 hereinafter. Said test procedure is analogous to the test procedures mentioned in official pharmacopoeias, e.g. the U.S. Pharmacopoeia XXII.

The person skilled in the art of developing pharmaceutical compositions is faced with the problem of making a solid dosage form suitable for oral administration so that the compound of formula (I) has an acceptable dissolution. Moreover, said person skilled in the art is bound by other limiting conditions. The pharmaceutical composition developed by him will be prepared on industrial scale and will have to satisfy the requirements of internal and external quality control.

Oral administration of nebivolol hydrochloride is impeded by the poor dissolution when in a normal crystalline form. In the course of the investigations towards improving the bioavailability of nebivolol hydrochloride, the product was micronized. Unfortunately, as can be seen from example 3, the dissolution of micronized nebivolol hydrochloride is even worse than nebivolol hydrochloride in normal crystalline form.

Unexpectedly however, it was found that when nebivolol hydrochloride in micronized form is formulated in a composition with art-known formulating agents as described hereinunder it has an appropriate dissolution and meets internal and external quality control requirements.

Hence, the present invention provides a particularly advantageous formulation of nebivolol hydrochloride. There is thus provided according to the invention a pharmaceutical composition having an appropriate dissolution, more particular a pharmaceutical composition for oral administration comprising a solid dosage form including nebivolol hydrochloride in micronized form.

Micronized forms of nebivolol hydrochloride may be prepared by micronization techniques known in the art, e.g. by milling in appropriate mills and sieving through appropriate sieves.

The specific area of said micronized material should at least amount to about $23 \times 10^3$ cm$^2$/g ($2.3 \times 10^3$ m$^2$/kg), preferably the specific area should amount to more than $25 \times 10^3$ cm$^2$/g ($2.5 \times 10^3$ m$^2$/kg), more preferably more than $28 \times 10^3$ cm$^2$/g ($2.8 \times 10^3$ m$^2$/kg), and most preferably more than $31 \times 10^3$ cm$^2$/g ($3.1 \times 10^3$ m$^2$/kg).

According to this invention the characteristics of the micronized nebivolol hydrochloride are as follows. At most 50% of the particles may have a diameter larger than 10 μm, i.e. the $DL_{50}$ has a maximum value of 10 μm. Preferably the $DL_{50}$ should amount to less than 8 μm. At most 10% of the particles may have a diameter larger than 20 μm, i.e. the $DL_{10}$ has a maximum value of 20 μm. Preferably the $DL_{10}$ should amount to less than 18 μm.

Compositions according to the present invention will preferably comprise pharmaceutically acceptable carriers and excipients, such as fillers e.g. lactose, sucrose, mannitol, maize starch, microcrystalline cellulose or calcium hydrogen phosphate; lubricants e.g. stearic acid, polyethylene glycol, magnesium stearate, talc or silica; disintegrants e.g. rice, potato or maize starch, sodium starch glycolate or croscarmellose sodium (i.e. sodium carboxymethylcellulose); binding agents e.g. pregelatinised maize starch, polyvinylpyrrolidone or hydroxypropylmethylcellulose and wetting agents e.g. sodium dioctylsulfosuccinate and Polysorbates.

Interesting fillers are lactose, sucrose or microcrystalline cellulose; preferably lactose and microcrystalline cellulose. Interesting lubricants are stearic acid, polyethylene glycol, hydrogenated vegetable oil, sodium stearyl fumarate or magnesium stearate, preferably magnesium stearate. Interesting disintegrants are rice, potato or maize starch, preferably croscarmellose sodium. Preferred binding agent is hydroxypropylmethylcellulose.

It was found that polysorbates were the wetting agents of choice. Interesting wetting agents are Polysorbate 20 (Tween 20®), Polysorbate 40 (Tween 40®), Polysorbate 60 (Tween 60®), Polysorbate 80 (Tween 80®), Polysorbate 65 (Tween 65®), Polysorbate 85 (Tween 85®). More interesting wetting agents are Polysorbate 20, Polysorbate 40, Polysorbate 60, Polysorbate 80. Preferred wetting agent is Polysorbate 80.

Interesting compositions comprise by weight based on the total weight of the composition:
nebivolol hydrochloride: from 1% to 4%
fillers: from 60% to 90%
disintegrants: from 3% to 10%
binding agents: from 0.5% to 5%
wetting agents: from 0.1% to 1.0 %

More interesting compositions comprise by weight based on the total weight of the composition.
nebivolol hydrochloride: from 1% to 4%
fillers: from 75% to 85%
disintegrants: from 4% to 8%
binding agents: from 1% to 3%
lubricants: from 0.4% to 0.9%
wetting agents: from 0.1% to 0.8%

Preferred compositions comprise by weight based on the total weight of the composition.
nebivolol hydrochloride: from 2% to 3%
lactose: from 55% to 65%
maize starch: from 15% to 25%
croscarmellose sodium: from 5% to 7%
hydroxypropyl methylcellulose: from 1% to 3%
polysorbate: from 0.1% to 0.5%
magnesium stearate: from 0.4% to 0.6%

For the preparation of compositions according to the invention micronized nebivolol hydrochloride is blended with suitable excipients and granulated. Preferably nebivolol hydrochloride will be granulated with the filler or fillers before admixture of the other excipients. Most preferably the fillers employed will be lactose and maize starch.

The ratio (w/w) of wetting agent/nebivolol hydrochloride is an important factor. In order to achieve a good dissolution the active ingredient has to be sufficiently wetted. On the other hand when the amount of wetting agent is too high in the composition, the resulting tablets do not have the appropriate hardness and consequently said tablets are not suitable for industrial production.

The ratio (w/w) of wetting agent/nebivolol hydrochloride may vary between about 0.025 and 0.5. Said ratio may preferably range from about 0.025 to about 0.3. More preferably said ratio ranges from about 0.04 to about 0.25. Most preferably said ratio ranges from about 0.06 to 0.1.

Tablets according to this invention may be right circular cylinders or may have a rod-like shape, the end surfaces of which may be flat or convex and the edges of which may be levelled. Said tablets may have lines or break-marks and may bear a symbol or other markings.

A further aspect of the invention provides a method of treating a patient suffering from conditions associated with coronary disorders and hypertension which comprises oral administration of a pharmaceutical composition comprising a solid dosage form comprising micronized nebivolol hydrochloride. It will be appreciated that the precise therapeutic dose of the active ingredient will depend in the age and condition of the patient and the nature of the condition to be treated and will be at the ultimate discretion of the attendant physician. However, in general effective doses for the treatment of conditions associated with coronary disorders and hypertension, will lie in the range of about 0.1 to about 50 mg, most preferably about 1 to about 10 mg, for example about 5 mg of the active ingredient per unit dose which could be administered in single or divided doses, for example, 1 to 4 times per day.

EXPERIMENTAL PART

Example 1: Preparation of Nebivolol Hydrochloride (±)-[2R*[1S*,5S*(S*)]]+[2R*[1S*,5R*(R*)]]-α,α'[iminobis(methylene)]bis[6-fluoro-3,4-dihydro-2H-1-benzopyran-2-methanol] (142 g) was converted into the hydrochloric acid salt in ethanol (1000 ml). The crystals were filtered off and crystallized from ethanol. The second fraction of the crystallization was recrystallized from ethanol, yielding 10.3 g (6.6%) of (±)-[2R*[1S*,5S*(S*)]]-α,α'[iminobis(methylene)]bis[6-fluoro-3,4-dihydro-2H-1-benzopyran-2-methanol]hydrochloride; mp. 224.9° C. nebivolol hydrochloride (crystalline compound 1).

Example 2: Micronization of Nebivolol Hydrochloride

A quantity of 11 kg of nebivolol hydrochloride was micronized using a Air Classifying Mill with a milling disc equipped with stones. The working speed is optimal at 13,500 revolutions per minute. When the particles are small enough they are taken up with the air stream and led to a wind sieve, where they are collected, yielding micronized compound 1.

Example 3: Dissolution Test

|  | specific area m²/kg | dissolution after 60 minutes |
|---|---|---|
| crystalline compound 1 | 0.226 × 10³ | 28.1% |
| micronized compound 1 | 3.012 × 10³ | 17.4% |

Example 4: Preparation of Tablets Containing Compound 1

| Composition of the final tablet: | | |
|---|---|---|
| nebivolol hydrochloride: | 5.45 mg | 2.40% |
| lactose: | 141.75 mg | 61.6% |
| maize starch: | 46.00 mg | 20.0% |
| croscarmellose sodium | 13.80 mg | 6.00% |
| colloidal anhydrous silica: | 0.60 mg | 0.26% |
| magnesium stearate | 1.15 mg | 0.50% |
| hydroxypropyl methylcellulose (Hypromellose) 2910 15 cps (*): | 4.60 mg | 2.00% |
| polysorbate 80: | 0.46 mg | 0.20% |
| microcrystalline cellulose: | 16.10 mg | 7.00% |

(*) Hypromellose is the British Approved Name as well as the recommended International Nonproprietary Name for hydroxypropyl methylcellulose. The classes of hydroxypropyl methylcellulose are distinguished by a four digit code, here 2910. The first two digits represent the approximate percentage composition of methoxyl groups, and the third and fourth digits the approximate percentage composition of hydroxypropyl groups. The indication "15 cps" refers to the viscosity of 15 centipoise mPa · s) of a 2% solution measured at 20° C.

Preparation of the binder solution 92 g of hydroxypropyl methylcellulose 2910 15 cps and 9.2 g polysorbate 80 were dissolved in 1,840 g demineralized water under magnetic stirring at a temperature of 90° C.

Preparation of the granulate 109 g nebivolol hydrochloride, 138 g croscarmellose sodium, 2,835 g lactose and 920 g of maize starch are mixed in a fluidized-bed granulator under a working pressure of 5–6 bar. The inlet air temperature is 60° C. The mixing process is continued up until the outlet air temperature has reached a temperature of 30° C. Subsequently, the binder solution is sprayed onto the powder mixture. After the spraying the granulate is dried with an inlet air temperature being 75° C.

Preparation of the compression mixture

The dried granulate, 322 g microcrystalline cellulose, 138 g croscarmellose sodium, 13 g colloidal anhydrous silica and magnesium stearate are sieved through a stainless-steel frame sieve (mesh: 0.95 mm) and are mixed in a planetary powder mixer until a homogeneous mixture is obtained.

Preparation of the tablets

From the above compression mixture tablets of 230 mg are prepared using a rotary tablet press.

Example 5: Dissolution Test

Preparation of the standard solution.

Approximately 54.5 mg of nebivolol hydrochloride was weighed accurately in a 50 ml volumetric flask. Said quantity of nebivolol hydrochloride was dissolved in methanol and diluted to volume (50 ml) with methanol.

Preparation of the reference solution.

A quantity of 5 ml of the standard solution (see above) was pipetted into a 500 ml volumetric flask. A placebo tablet was added as well as 300 ml hydrochloric acid 0.1N. This solution was heated to 37° C. and shaken mechanically for 30 minutes. The solution was further diluted to a volume of 500 ml with hydrochloric acid 0.1N. Subsequently the solution was filtered through a 15 μm filter.

Preparation of the sample solution.

A tablet comprising micronized nebivolol hydrochloride (prepared as described in example 4) was placed into a dissolution vessel of the Paddle apparatus as described in the European Pharmacopoeia with a rotation speed set at 50±2 revolutions per minute and the dissolution medium being hydrochloric acid 0.1N and a fixed temperature of 37° C.±0.5° C.

Measurement

After 45 minutes of stirring in the dissolution vessel a sample of 6 ml was withdrawn from the dissolution vessel and filtered through a 15 μm reagent filter. The absorbance of the sample was measured using a spectrophotometer (after a second filtration through a 0.2 μm filter) at the maximum near 280 nm, in a 10 mm-cell against a "blank solution" consisting of hydrochloric acid 0.1N.

Calculation $$A_s corr. = \frac{54.5 A_s}{W_s}$$

Where $A_s$=measured absorbance of the 'reference solution'.

$W_s$=weighed quantity, in mg, of nebivolol hydrochloride reference material $$\% \text{ dissolved} = \frac{A_{45}}{A_s corr.} \cdot 100$$

Where $A_{45}$=measured absorbance of the 45-minutes sample

Tablets as prepared in Example 4 showed a dissolution of 75%, i.e. 75% dissolved, after 45 minutes.

Example 6: Comparison of Dissolution of Tablets Comprising Crystalline Versus Micronized Nebivolol

| Tablet 1 | Tablet 2 | |
|---|---|---|
| compound 1 crystalline | compound 1 microfine | 5.45 mg |
| polysorbate 80 | polysorbate 80 | 2.30 mg |
| hydroxypropyl methylcellulose 2910 15 cps | hydroxypropyl methylcellulose 2910 15 cps | 4.60 mg |
| lactose | lactose | 139.91 mg |
| maize starch | maize starch | 46.00 mg |
| acdisol | acdisol | 13.80 mg |
| microcrystalline cellulose | microcrystalline cellulose | 16.10 mg |
| colloidal anhydrous silica | colloidal anhydrous silica | 0.69 mg |
| magnesium stearate | magnesium stearate | 1.15 mg |

The dissolution rates fo the tablets were measured using an analogous procedure as described in Example 5. The tablets were placed in a dissolution vessel of the Paddle apparatus with a rotation speed set at about 100 revolutions per minute, the dissolution medium being artificial gastric juice and the temperature fixed at 37° C. The dissolution rate of the tablet comprising crystalline nebivolol (tablet 1) amounted to less than 50% after 45 minutes, while the dissolution rate of the tablet comprising micronized nebivolol (tablet 2) amounted to more than 75% after 45 minutes.

We claim:

1. A pharmaceutical composition comprising a pharmaceutically acceptable carrier and as active ingredient nebivolol or a pharmaceutically acceptable salt thereof characterized in that the active ingredient is in a micronized solid form and wherein the pharmaceutically acceptable carrier comprises a filler, lubricant, disintegrate, binding agent and wetting agent.

2. A pharmaceutical composition as claimed in claim 1 wherein the pharmaceutical composition is a solid pharmaceutical composition.

3. A pharmaceutical composition as claimed in claim 1 or 2, wherein the active ingredient is a micronized form of nebivolol hydrochloride.

4. A pharmaceutical composition as claimed in claim 3, wherein the micronized form of nebivolol hydrochloride has a specific surface area of at least $23 \times 10^3$ cm$^2$/g ($2.3 \times 10^3$ m$^2$/kg).

5. A pharmaceutical composition as claimed in claim 3, wherein said pharmaceutical composition comprises 1 to 4% of a micronized form of nebivolol hydrochloride.

6. A pharmaceutical composition as claimed in claim 3, wherein said pharmaceutical composition further comprises a Polysorbate as a wetting agent and wherein the ratio (w/w) of Polysorbate to nebivolol hydrochloride ranges from 0.025 to 0.5.

7. A pharmaceutical composition as claimed in claim 2, wherein said pharmaceutical composition is a tablet.

8. A pharmaceutical composition as claimed in claim 3, wherein said pharmaceutical composition is a tablet substantially having the following composition:

| | |
|---|---|
| nebivolol hydrochloride: | 2.40% |
| lactose: | 61.6% |
| maize starch: | 20.0% |
| croscarmellose sodium | 6.00% |
| colloidal anhydrous silica: | 0.26% |
| magnesium stearate | 0.50% |
| Hypromellose 2910 15 cps: | 2.00% |
| Polysorbate 80: | 0.20% |
| microcrystalline cellulose: | 7.00% |

9. A tablet as claimed in claim 7, characterized in that it has a dissolution of 75% after 45 minutes.

10. A micronized form of nebivolol hydrochloride having a specific area of at least $23 \times 10^3$ cm$^2$/g.

11. A pharmaceutical composition as claimed in claim 1, wherein the filler is selected from the group consisting of lactose, sucrose, mannitol, maize, starch, microcrystalline cellulose and calcium hydrogen phosphate.

12. A pharmaceutical composition as claimed in claim 1, wherein the lubricant is selected from the group consisting of stearic acid, polyethylene glycol, hydrogenated vegetable oil, sodium stearyl fumarate, magnesium stearate, talc and silica.

13. A pharmaceutical composition as claimed in claim 1, wherein the disintegrant is selected from rice, potato or maize starch, sodium starch glycolate, and croscarmellose sodium.

14. A pharmaceutical composition as claimed in claim 1, wherein the binding agent is selected from the group consisting of pregelatinized maize starch, polyvinylpyrrolidone and hydroxpropyl methylcellulose.

15. A pharmaceutical composition as claimed in claim 1, wherein the wetting agent is sodium dioctylsulfosuccinate or a polysorbate.

16. A pharmaceutical composition as claimed in claim 1, wherein the filler is lactose, sucrose, mannitol, maize starch, microcrystalline cellulose or calcium hydrogen phosphate; the lubricant is stearic acid, polyethylene glycol, hydrogenated vegetable oil, sodium stearyl fumarate, magnesium stearate, talc or silica; the disintegrant is rice, potato or maize starch, sodium starch glyolate or croscarmellose sodium; the binding agent is pregelatinized maize starch, polyvinylpyrrolidone or hydroxy propylmethylcellulose; and the wetting agent is sodium dioctyl sulfosuccinate or a polysorbate.

17. A pharmaceutical composition as claimed in claim 11, wherein the filler is lactose, sucrose or microcrystalline cellulose; the lubricant is stearic acid, polyethylene glycol, hydrogenated vegetable oil, sodium stearyl fumarate or magnesium stearate; the disintegrant is rice, potato or maize starch or croscarmellose sodium; the binding agent is hydroxypropylmethyl cellulose; and the wetting agent is a polysorbate.

18. A pharmaceutical composition as claimed in claim 1, wherein the ratio (w/w) of wetting agent to nebivolol or pharmaceutically acceptable salt thereof is in the range of about 0.025 to 0.5.

19. A pharmaceutical composition as claimed in claim 18, wherein the ratio (w/w) of wetting agent to nebivolol or pharmaceutically acceptable salt thereof ranges from about 0.025 to about 0.3.

20. A pharmaceutical composition as claimed in claim 19, wherein the ratio (w/w) of wetting agent to nebivolol or pharmaceutically acceptable salt thereof ranges from about 0.04 to about 0.25.

* * * * *

UNITED STATES PATENT AND TRADEMARK OFFICE
CERTIFICATE OF CORRECTION

PATENT NO. : 5,759,580
DATED : June 2, 1998
INVENTOR(S) : Jans et al.

It is certified that error appears in the above-identified patent and that said Letters Patent is hereby corrected as shown below:

Column 7,
Line 12, change "disintegrate" to -- disintegrant --.

Signed and Sealed this

Twenty-sixth Day of October, 2004

JON W. DUDAS
*Director of the United States Patent and Trademark Office*